United States Patent [19]

Cassou et al.

[11] 4,368,732

[45] Jan. 18, 1983

[54] ARTIFICIAL INSEMINATION DEVICE FOR AVICULTURE

[75] Inventors: Bertrand Cassou, Saint Symphorien les Bruyeres, 61300 L'Aigle, France; Lucien Bonnet, Monnaie, France; Jean P. Brillard, Monnaie, France; Jacques Courtemanche, Monnaie, France; Michel de Reviers, Monnaie, all of France

[73] Assignees: Bertrand Cassou; Maurice Cassou; Robert Cassou, all of L'Aigle, France

[21] Appl. No.: 250,958

[22] Filed: Apr. 1, 1981

[30] Foreign Application Priority Data

Jun. 16, 1980 [FR] France ................................ 80 13332

[51] Int. Cl.³ ................................................ A61M 1/00

[52] U.S. Cl. ..................................................... 128/235

[58] Field of Search ............... 128/235, 220, 221, 234, 128/215, 213, 218 P, 218 F

[56] References Cited

U.S. PATENT DOCUMENTS

| | | | |
|---|---|---|---|
| 2,750,943 | 6/1956 | Dann | 128/235 |
| 2,942,603 | 6/1960 | Geyer | 128/235 |
| 3,400,716 | 9/1968 | Schultz | 128/235 X |
| 3,682,175 | 8/1972 | Halter | 128/235 X |

*Primary Examiner*—John D. Yasko

*Attorney, Agent, or Firm*—James C. Wray

[57] ABSTRACT

This device is of the type comprising a hollow cylindrical body for receiving at one end a semen reservoir-tube with which are associated means for maintaining the reservoir-tube on the body. Also provided in the body is a slidably mounted plunger-rod which projects from the end of the body opposed to the reservoir-tube. This plunger-rod is adapted to expel semen contained in the reservoir-tube, the plunger-rod cooperating with means for advancing the plunger-rod in a step-by-step manner and actuated by a periodic actuating means.

The step-by-step advancing means comprise an advancing element which is provided with an aperture and is mounted with a small clearance on the plunger-rod. This element bears, by the side thereof opposed to the reservoir-tube, on one hand, against a fixed stop member located to one side of the plunger-rod and, on the other hand, against a member which constitutes the periodic actuating means and which is movable in translation in a direction parallel to the plunger-rod between a first position which is situated in confronting relation to the fixed stop member and a second position which is offset toward the reservoir-tube. Return means are provided for returning the actuating means to the first position thereof.

20 Claims, 5 Drawing Figures

ARTIFICIAL INSEMINATION DEVICE FOR AVICULTURE

The present invention relates to artificial insemination devices for small animals, in particular for farmyard birds (pigeons, chickens, guinea-fowl), termed "machine-guns," which are of the type comprising a cylindrical body in which a plunger-rod is slidably mounted, this plunger-rod cooperating with step-by-step advancing means actuated by a periodic actuating means which is provided with means for returning it to a position of rest.

Such a "machine-gun" permits carrying out, with a given volume of semen (or other product to be injected) contained in the reservoir-tube, a plurality of successive injecting operations, each of which utilizes only a given fraction or dose which is known and perfectly determined so that it is possible to immediately inseminate a plurality of animals of small size.

Devices of the considered type are already known, for example from French Pat. No. 1,525,336, in which step-by-step advancing is achieved by notches which are arranged in a diametrally alternating manner on the length of the plunger and cooperate with actuating means formed by a rotary thrust member of hairpin shape which is each time turned through 180° so as to release it from one of the notches and provide a stop member for the following notch.

However, various difficulties are encountered in the operation of such a device, since the thrust member is hardly convenient to displace and is sometimes liable to block the plunger-rod.

This is why an object of the present invention is to provide a device which is perfectly reliable in its actuation.

The invention provides a device of the aforementioned type with which there are associated support means which comprise a support unit proper on which is slidably mounted a unit for fixing the body of the device, on which unit said body is so disposed that the plunger-rod is parallel to the axis of sliding, the fixing unit being rigid with a thrust assembly which has a thrust member proper disposed along said sliding direction roughly in the region of the orifice of the semen reservoir-tube, whereas the periodic actuating means has a part which projects in the position of rest from the rear of the body of the device and is located in confronting relation to a supporting stop member rigid with the support unit.

With this arrangement, it is sufficient to shift the actuating means between the two positions thereof, for the advancing means, which is consequently inclined relative to the plunger-rod and is locked to the plunger-rod, to drive the latter through a segment of travel corresponding to the injection of an elementary dose of semen, it being possible to repeat this operation a number of times.

In a particularly advantageous embodiment, the step-by-step advancing means may be arranged to comprise anti-return means which oppose a return of the plunger-rod when the actuating means is returned to its first position.

Also, preferably, the cylindrical body may be rigid with a case which extends the body on the side thereof opposed to the reservoir-tube and has the plunger-rod extending therethrough and encloses the advancing means and carries the various stop members so that the device is rendered extremely easy to handle and actuate.

Such a so-called "machine-gun" device permits, with the use of a given volume of semen contained in the reservoir-tube, effecting a plurality of successive insemination operations each of which uses only a given fraction or does which is known and perfectly determined (10, 20 or 50 microliters), so that it is possible to inseminate a number of animals of small size in succession.

In the particular embodiment described hereinbefore, the periodic actuating means is arranged in the form of a trigger which is accessible from the exterior in front of a handle rigid with the body and which can consequently be actuated manually.

Now, if suitable results are to be obtained, these known devices can only be used by a team of two inseminators, one of whom seizes the animal and effects the eversion of the vagina of the latter so as to maintain it then in this position with both hands, while the other holds the device by its handle and gently inserts in the vagina the flexible protective sheath, which surrounds and usually maintains the semen reservoir-tube on the body of the device, and then actuates the trigger, the movement of which causes a partial displacement of the plunger-rod and consequently the ejection of a dose of semen into the vagina of the animal, it being possible to repeat this operation on other animals until the emptying of the reservoir which must then be replaced.

However, the insemination rate is in this case limited by the fact that the insemination needs the presence of a team of two persons.

Consequently, another object of the invention is to provide a device of the considered type which can be used by a single person at the same rate of insemination as with known devices while of course giving results which are just as good.

For this purpose, the invention also provides a device of the considered type with which there is associated a support comprising a support unit proper on which is slidably mounted a fixing unit for the body of the device on which unit said body is so disposed that the plunger-rod is parallel to the axis of sliding, the fixing unit being itself rigid with a thrust unit which has a thrust member proper disposed along said direction of sliding, roughly in the region of the orifice of the semen reservoir-tube, whereas the periodic actuating means has a part which, in the position of rest thereof, projects from the rear of the body of the device and is located in confronting relation to a supporting stop member rigid with the support unit.

With this arrangement, the inseminator, who now has no need of any assistance, siezes the animal, effects in the usual way the eversion and then, while holding the animal in both hands, presents the animal in front of the device and pushes the animal in such manner as to cause the end of the sheath to enter the vagina to a depth of about, for example, 3 centimeters; when this positioning has been effected, the back of one of the hands of the operator comes in contact with the thrust member of the auxiliary support and he can then continue to simultaneously push the animal and the thrust member, since the latter carries along therewith the machine-gun rearwardly with respect to the support. During this rearward movement, as the rear part of the actuating means bears against the stop member of the support, the resulting relative movement between this actuating means and the body of the device causes the actuation of the means for advancing the plunger-rod and consequently the injection of a dose of semen into the vagina of the animal.

The operator removes the animal and the device is ready for a new insemination.

Particularly advantageously, it might be arranged, on one hand, that the thrust unit be mounted to be movable in translation relative to the fixing unit along said axis of sliding, detachable securing means being provided between the two units and, on the other hand, that this thrust unit be also mounted to be movable relative to the fixing unit in a transverse direction perpendicular to the plunger-rod, it then being possible to mount the thrust member proper to be movable transversely of the plunger-rod.

These various arrangements permit a perfect adjustment of the position of the thrust member so that the operator can actuate the device with maximum facility. Preferably, the plane of the plunger-rod may also be disposed above the sliding axis and, moreover, the support unit may comprise a part which is orientable about a horizontal axis, which also facilitates the actuation of the device.

In a particular embodiment of the invention, the fixing unit may comprise a rod which is disposed along the sliding axis, slidably mounted at one end in a tube which is part of the support unit, and rigid at the other end with the thrust unit, while preferably this fixing unit may comprise a block which serves to fix the body of the device and is rigid with the sliding rod but disposed outside the support tube, it being possible to arrange that the thrust unit may itself comprise a block which is slidably and rotatably mounted on the end of the sliding rod and fixed to the latter by a securing or set screw.

These particular features of construction result in a simple manufacture, easy assembly and perfect adjustment.

Further features and advantages of the invention will be apparent from the ensuing description which is given merely by way of example with reference to the accompanying drawings in which.

Figure 1:
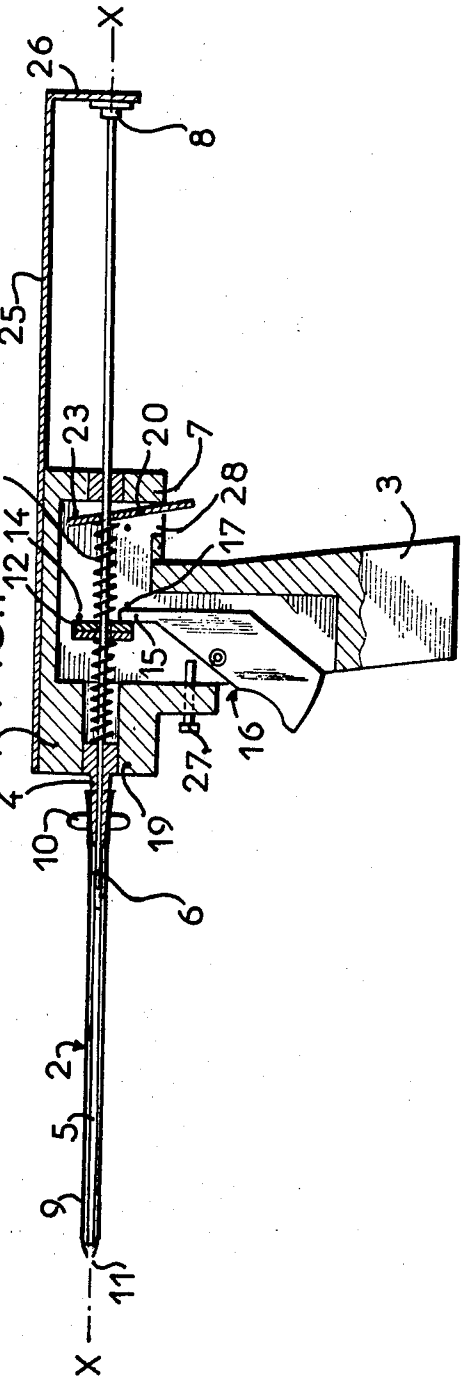
FIG. 1 is a sectional view of a device according to a particular embodiment of the invention.

The illustrated device is in the form of a gun comprising a case 1 from one end of which projects a barrel-shaped unit 2 disposed on an axis X—X, this body 1 being rigid with a handle or grip 3 which is disposed laterally with respect to the axis X—X.

The barrel-shaped unit 2 comprises a frustoconical end member 4 having a cylindrical bore which is fixed to the case 1 and is adapted to act as a support for a semen reservoir-tube 5. The bore of the end member 4 receives a plunger-rod 6 which is slidable therein and extends through the case 1 and beyond the end 7 of the latter opposed to the end member 4. At its outer end, this plunger-rod has a head 8 and its inner end is adapted to expel from the reservoir-tube 5 the semen contained in the latter. The assembly comprising the reservoir-tube 5 and the body 4 is surrounded by a flexible protective sheath 9 which is maintained on the body 4, in the vicinity of the case 1, by a gripping ring 10. The sheath defines at the opposite end thereof an end axial orifice 11 for discharging the semen.

Disposed inside the case 1 and the handle 3 are means for achieving a step-by-step advance of the plunger-rod, means for periodically actuating or triggering this advance and anti-return means.

The step-by-step advancing means comprises an advancing element comprising two plates 12 which have apertures 13 by which the plates are mounted on the plunger-rod 6 with a slight clearance. The plate 12 remote from the barrel 2 bears against a first fixed stop member 14 which is located to one side of the plunger-rod in a centre cavity of the case. This plate 12 also bears, on the opposite side of the plunger-rod to the stop member 14, against a finger member carried by a trigger 16 constructed in the form of a double-arm lever and pivotally mounted inside the handle 3 so that the arm opposed to that which carries the finger member 15 extends out of the handle and can be actuated by hand. The finger member 15 constitutes a periodic actuating means which, owing to the rotation of the trigger 16, is movable roughly in translation parallel to the plunger-rod between a first position (shown in FIGS. 1 and 3) in which the finger member is contained in the same plane perpendicular to the rod 6 as the stop member 14 and a second position in which the finger member is offset toward the barrel 2.

Figure 3:
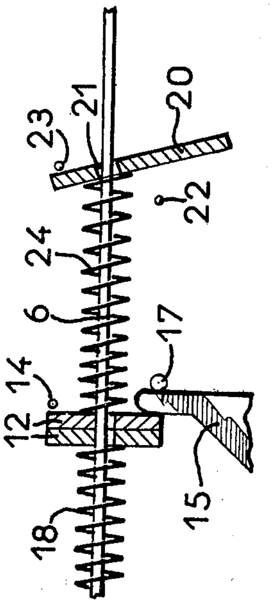
FIGS. 2 and 3 are partial views of this device illustrating two positions in the operation thereof.

A second fixed stop member 17 is disposed on the case 1 on the opposite side of the rod 6 to the first stop member 14 and on the opposite side of the plates 12 to the finger member 15 so that the latter bears against this stop member 17 when it is in the first position shown in FIG. 1. As shown in FIG. 3, in this position, the plates 12 are perpendicular to the axis X—X and they are held in this position by a compression spring 18 which is placed between the second plate 12 and the front end 19 of the case 1. Owing to the clearance provided for the apertures 13, the plates are not jammed or locked on the rod in this perpendicular position.

Figure 2:
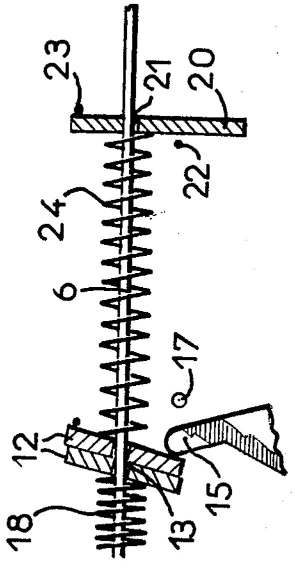

The anti-return means comprises another plate 20 which is disposed in the case adjacent to the rear end 7 thereof and also has an aperture 21 by which it is mounted on the rod 6 with a small clearance. This plate 20 bears by the side thereof facing the barrel 2 against another fixed stop member 22 located on the same side of the rod 6 as the stop member 17 and fixed to the case 1. This plate 20 also bears by its opposite side against another fixed stop member 23 which is located on the same side of the rod 6 as the stop member 14 and the two stop members 22 and 23 are axially offset from each other so that the plate 20 is in contact with each of them when it is in a vertical position, as shown in FIG. 2. Associated with this plate is a second compression spring 24 which is disposed between the plates 12 and the plate 20 and surrounds the plunger-rod in the same way as the first spring 18. The length and the hardness of this spring 24 are such that it is constantly compressed between the advancing plates 12 and the anti-return plate 20, however in such manner that the plate 20 can remain perpendicular to the rod 6 when the plates 12 are inclined with respect to the rod under the action of the trigger 16 whereas, on the other hand, when the plates 12 have returned to a position in which they are perpendicular to the rod 6, it is the plate 20 which is inclined under the action of the compression of the spring 24.

The case 1 carries a rearwardly-extending strip 25 which is fixed thereto and has at the free end thereof a flange 26 which is perpendicular to the axis X—X and constitutes an end-of-travel stop member for the head 8 of the plunger-rod. The travel of the head 8, between this stop member 26 and the other end-of-travel stop member formed by the rear end 7 of the case, substantially corresponds to the length of the reservoir-tube or "straw" 5 so that, when the head 8 is in contact with the stop member 26, the end of the plunger-rod 6 is located just at the entrance of the straw 5, while, when this head 8 is put in contact with the end 7, the plunger-rod 6 has travelled completely through the straw 5 and has expelled in the known manner the semen contained in the straw through the orifice 11 of the sheath 9, the plunger-rod acting through the piston-plug which closes this straw at the end thereof facing the plunger-rod 6.

The handle 3 carries, adjacent the barrel 2, a screw 27 which is in confronting relation to the arm of the lever of the trigger 16 which carries the finger member 15 so as to form an adjustable stop member for the travel of this lever arm. This adjustment of the screw 27 must allow the actuating finger member 15 sufficient travel so that, when the trigger 16 has come in contact with the stop screw 27, the finger member 15 has sufficiently inclined the plates 12 to ensure that the edges of the apertures 13 of these plates grip the rod 6 in the manner of jaws (as shown in FIG. 2).

The device just described is used in the following manner:

At the moment of use, the rod 6 is urged rearwardly so that the head 8 comes in contact with the rear stop member 26. A straw 5 is then placed on the frustoconical end member 4 and maintained in position by slipping over this straw and this end member the sheath 9 which is secured to the end member by the ring 10. It will be understood that the end of the straw 5, with its plug, which must be located in confronting relation to the orifice 11 of the sheath has been cut off. The device is thus in the position illustrated in the FIG. 3.

The trigger 16 is then depressed so that the actuating finger member 15 inclines the plates 12, the latter thus becoming "jammed" on the plunger-rod 6. The finger member thus drives the rod 6 in the forward direction through the plates 12 until the trigger 15 abuts the stop screw 27. In the course of this movement, the rear plate 20 has placed itself perpendicular to the rod and has remained in this position throughout the travel of the finger member 15 and consequently does not oppose the displacement of the rod 6.

The displacement of the rod 6 has resulted in the expulsion of a perfectly determined amount or dose of the semen or other product contained in the straw 5.

If the trigger 16 is then released, the spring 18 returns the plates 12 to a position perpendicular to the rod and these plates urge the second spring 24 rearwardly and the latter brings the plate 20 to an inclined position in which (as shown in FIG. 3) the edges of the aperture 21 in turn grip the rod 6 in the manner of jaws. This immobilization of the rod 6 by the plate 20 thus opposes a return of the rod 6 and enables the latter to be maintained in the same position until the following operation for the ejection of a new dose of semen or other product.

Consequently, it is possible to repeat this double movement, comprising an advance of the plunger-rod and a return of the trigger, for injecting all of the product contained in this straw in the form of successive doses of perfectly determined volume.

Once the whole of the product has been ejected, the rod 6 has travelled through practically the whole of the straw and the rod head 8 has abutted the end 7 of the case. In view of the fact that the plate 20 is made long enough to laterally project from the case 1 through an opening 28 provided for this purpose, it is possible to press on this plate in the forward direction so as to render it also perpendicular to the axis X—X which is already the position of the plates 12 (shown in FIG. 3) so that it is possible to return the plunger-rod 6 rearwardly by means of the head 8 until the latter abuts the stop member 26. The device is thus ready for placing in position a new straw and effecting a new series of injections.

By modifying the adjusted position of the stop screw 27, the extent of the repeated travels of the rod 6 may be made different so that variable doses may be injected into the animals. These doses may depend on the product or the considered breed.

It must be understood that various modifications may be made in the embodiment just described without departing from the scope of the invention as defined in the claims. Thus, in particular, the gripping ring 10 may be dispensed with if there is provided on the frustoconical end member 4 a spiral-shaped rib on which the flexible sheath 9 fastens itself.

Figure 4:
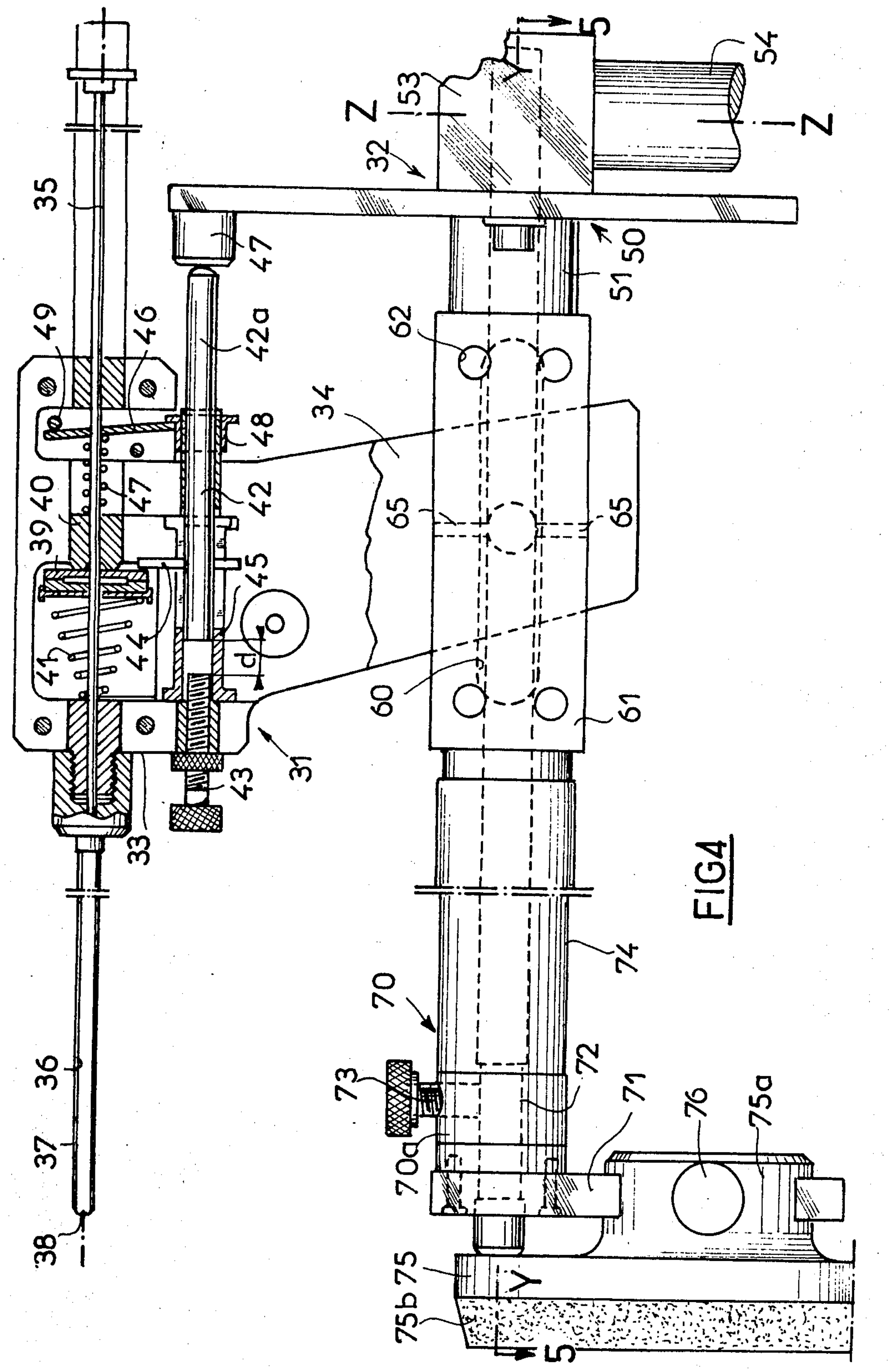
FIG. 4 is a top plan view of a device according to a particular embodiment of the invention.
Figure 5:
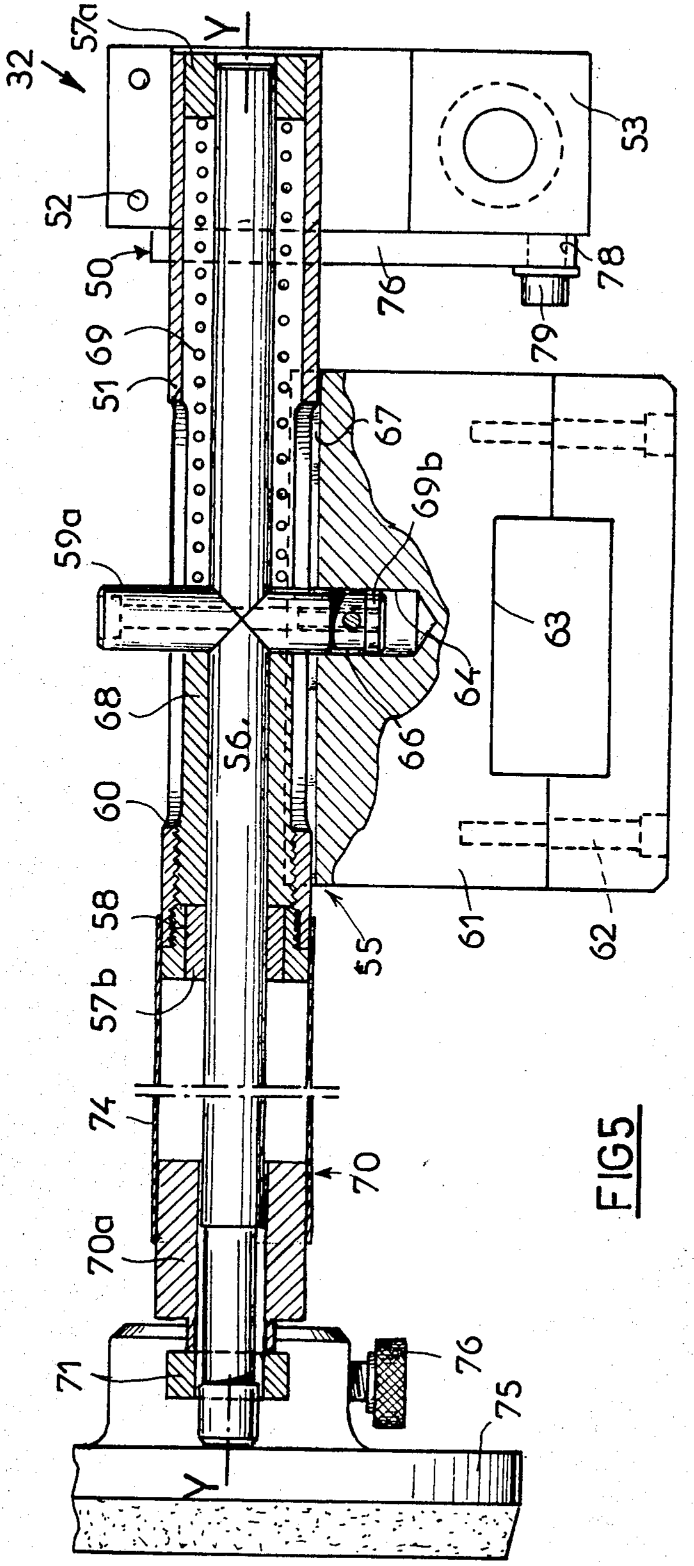
FIG. 5 is a rear view of the device of FIG. 4 taken along line 2—2 and in which the "machine-gun" device has been withdrawn.

The device shown in FIGS. 4 and 5 comprises, on one hand, an artificial insemination device proper 31, termed "machine-gun" and, on the other hand, a support 32.

The device 31 comprises a body 33 similar to that of a gun and having a handle 34 extending transversely of an axis X—X along which a plunger-rod 35 is mounted to be slidable, one end of the rod projecting from the rear of the body 33 while the other front end thereof is capable of penetrating the interior of a reservoir-tube 36 secured to the front of the body 33, this reservoir-tube being maintained on the body by means of a flexible protective sheath 37 having an end orifice 38.

The body 33 encloses step-by-step advancing means constituted by two plates 39 which are provided with apertures and are mounted on the plunger-rod with a slight clearance and are maintained in a rear position against a central stop member 40 of the body (that rod 35 extends through) under the action of a return spring 41 which surrounds this rod 35.

Arranged parallel to the axis X—X between the rod 35 and the handle 34 is an actuating rod 42 which is slidably mounted in the body 33 so as to project at one end 42*a* from the rear of the body while the other end of the rod 42 located within the body is in facing relation to a coaxial stop member formed by a screw 43 which is screwthreadedly engaged in a tapped hole in the body and has a head located outside the body. The rod 42 carries a transverse finger member 44 which extends through an opening in a sleeve 45 which is fixed to the body 33 and acts as a guide for the rod 42 and also projects from the rear of the body so that the end of the finger member 44 is located at the rear of the plates 39.

Disposed at the rear of the stop member 40 and also within the body 33 is an anti-return plate 46 which is also provided with an aperture and mounted on the rod 35 and is normally made to bear rearwardly, under the action of a return spring 47 disposed around the rod 35, on one hand, against a collar 48, slidably mounted on the sleeve 45 at the rear of the body 33, and, on the other hand, against a fixed stop member 49 located on the other side of the rod 35 to the collar 48 but with a slight forward offset relative to the latter so that this plate is inclined with respect to the rod 35 and consequently immobilizes the latter owing to the jamming action of the edge of its aperture against the rod 35 which prevents any rearward movement of the latter.

The support 32 comprises a support unit proper 50 formed by a tube 51 having an axis Y—Y parallel to the axis X—X and clamped at the rear end thereof by screws 52 between two jaws of a support block 53. The latter is rigid with the end of a tube 54 which is disposed on a horizontal axis Z—Z perpendicular to the axis Y—Y and extends away from the device 31, this tube 54 being mounted to pivot about the axis Z—Z on a fixed frame (not shown), such as a tripod, adapted to bear on the ground so that it is possible to orient the tube 51 upwardly or downwardly with respect to the normal horizontal position of the axis Y—Y, the tube being held in the chosen position by securing means such as screws (not shown).

Mounted on the support tube 51 to be slidable along the axis Y—Y is a fixing unit 55 which comprises a rod 56 slidably mounted in two bearings, namely a bearing 57*a* disposed at the rear end of the tube 40 and a bearing 57*b* inside a bored nut 58 which is fixed to the front end of the tube 51. The rod 56 carries, roughly mid-way of the length thereof and outside the block 53, two rod sections 59*a* and 59*b* which are fixed thereto and are perpendicular to the axis Z—Z so as to form with this rod a cross-shaped element two arms of which are slidable along the axis Y—Y in openings 60 formed in the tube 51. The upwardly extending arm 59*b* is rendered rigid with a fixing block 61 which has a parallelepipedic shape and is oriented upwardly and is formed by two parts which may be united by screws 62 and define therebetween a clamping passage 63 for receiving the handle 34 of the device 31 the section of which it roughly possesses. The block 61 is secured to the arm 59*b* by means of an aperture 64 in the block in which this arm is engaged, the arm being secured by two clamping screws 65 which are capable of bearing against a groove 66 of the arm 59*b* and are disposed parallel to the axis Z—Z. The side 67 of the block 61 facing the tube 51 has the shape of a sector of a cylinder so as to be capable of sliding longitudinally on this tube. The fixing unit comprising the rod 56 and the block 61 is urged against a cylindrical spacer member 68, bearing against the front bearing 57*b*, under the action of a return spring 69 which bears against the rear bearing 57*a*.

This fixing unit is rigid with a thrust unit 70 mounted on the front end of the rod 56 which extends beyond the bearing 57*b* to an extent equal to at least the extent of the tube 51. This unit comprises a hollow cylindrical member 70*a* having an axis Y—Y on the front end of which there is screwed a transverse bar 71 which is disposed on the same side as the tube 54, the assembly comprising the member 70*a* and the bar 71 being slidably mounted on the end of the rod 56 which has a groove 72 against the bottom of which is capable of bearing a set-screw 73 which is perpendicular to the rod 56 while a thin cylindrical member 74 connects the member 70*a* to the tube 51 in such manner as to act as a protective cover for the rod 56. Slidably mounted on the transverse end of the bar 71 is a hub-shaped member 75*a* provided at the rear of a disc 75 which is contained in a plane perpendicular to the axis Y—Y and disposed in front of the end of the rod 56 which extends through the bar 71, the hub 75*a* being capable of being held in position on the bar 71 by means of an adjusting screw 76 perpendicular to the latter. The disc 75 acts as a thrust member proper and is provided for this purpose with a flexible covering formed, for example, by an adhered foam material 75*b*.

Pivotally mounted on the support tube 51 and applied against the front side of the block 53 is a plate 76 which is perpendicular to the axis Y—Y and carries on an edge portion a stop member 77 which is disposed axially in confronting relation to the rear end 42*a* of the actuating finger member or rod 42 of the device 31, another edge portion of this plate 76 defining an oblong adjusting opening 78 in which is movable an adjusting and fixing screw 79 which is fixed in the block 53 perpendicular to the plate 76 so as to allow a slight rotation of the plate 76 about the tube 71 for bringing the stop member 77 exactly in facing relation to the rod 42.

In the position of use, the device 31 is consequently held in the fixing block 61 by the handle 34 of the device so that the axis X—X of the plunger-rod is located, on one hand, at a certain lateral distance from the thrust member 75 and, on the other hand, at a certain vertical distance above the latter, while the orifice 38 of the sheath 37 is slightly set back from this disc 75. Further, the rear end portion 42*a* of the actuating rod 42, whose lateral finger member 44 is located just to the rear of the plates 39, bears against the stop member 77 of the support while the front end thereof is disposed at a certain distance d from the end of the screw 43.

The device just described operates in the following manner:

The inseminator takes hold of the animal and, after having effected the eversion of the vagina, gently brings the latter in front of the flexible sheath 37 and inserts the end of the sheath into the vagina to a depth of about 3 centimeters. In this position, the back of the right hand of the operator practically comes in contact with the thrust member 75. Up to this moment, the assembly comprising the device 31 and the support 32 has undergone as yet no displacement and only the animal has been engaged on the end of the sheath 37.

The operator then continues to gently push the animal he is holding while simultaneously bearing on the thrust member 75 with the back of his hand. This movement of the thrust member is transmitted through the thrust unit comprising the bar 71 and the member 70*a* to the fixing unit comprising the rod 56 and the block 61 so that this movement is also transmitted through the handle 34 to the whole of the device 31. In this simultaneous rearward movement of the thrust member 75 and the device 31, the body 33 of the latter is urged rearwardly with respect to the rod 42 which is maintained stationary since it bears against the stop member 77 of the support 32.

Owing to this relative movement of the body 33 and the rod 42, the plates 39 are made to assume an inclined position under the action of the transverse finger member 44 so that, owing to the jamming action exerted by the central apertures of the plates on the rod 35, these plates are rendered rigid with this rod and the assembly is maintained stationary by the finger member 44 while the body 33 of the device continues to move rearwardly. This movement of the rod 35 with respect to the device causes a dose of semen contained in the reservoir-tube 36 to be ejected into the vagina of the animal. This ejection corresponds to the travel d which is allowed until the screw 43 comes in contact with the rod 42. The dose ejected is therefore a function of this travel d which is adjustable by means of the adjusting screw 43.

This travel is extremely short, for example of the order of 6 millimeters, so that the movement produced by the inseminator on the thrust member 75 is extremely small and is interrupted as soon as the ejection has occurred, upon which the inseminator removes the animal from the device by a reverse movement.

This operation needs only one inseminator and may be repeated several times on different animals until the reservoir-tube is empty, the rod having penetrated the reservoir-tube up to the end of the latter. The rod 35 can be returned rearwardly, notwithstanding the presence of the anti-return plate 46, by urging the collar 48 on the sleeve 45 forwardly.

To achieve maximum efficiency, the inseminator may perfectly adjust the position of the thrust member 75 with respect to the end 38 of the sheath 37 in three directions in space, since, by releasing the screw 73, he can slide the thrust unit along the rod 56 and also orient it about this rod and since, by releasing the screw 76, he can slide this thrust member along the bar 71.

Having now described our invention what we claim as new and desire to secure by Letters Patent is:

1. An artificial insemination device for small animals, comprising a hollow cylindrical body, a plunger-rod slidably mounted in the body and projecting from a first end of the body, a periodic actuating means, a step-by-step advancing means cooperative with the plunger-rod and comprising an advancing element which is provided with an aperture and is mounted on the plunger-rod with a small clearance between the advancing element aperture and the plunger-rod and which bears against the periodic actuating means, which actuating means is mounted to be movable in translation relative to the body in a direction parallel to the plunger-rod between a first position and a second position, return means cooperative with the actuating means to return the actuating means to said first position, the hollow cylindrical body being adapted to receive at a second end thereof opposed to said first end a semen reservoir-tube, means associated with said second end of the body for maintaining the reservoir tube on the body, a stop means mounted to be adjustable in position relative to the body in a direction substantially parallel to the plunger-rod, said actuating means being in bearing relation to said stop means in said second position.

2. A device according to claim 1, comprising a first fixed stop means mounted on the body laterally to one side of the plunger-rod, the advancing element bearing by a side thereof remote from said second end of the body against the first fixed stop means and bearing, on an opposite side of the plunger-rod to said first fixed stop means, against the periodic actuating means which, in said first position, is located in confronting relation to the first fixed stop means and, in said second position, is offset toward said second end of the body.

3. A device according to claim 2, wherein the return means comprises a spring which bears against a side of the advancing element remote from said first fixed stop means and the actuating means.

4. A device according to claim 2, comprising a second fixed stop means disposed on a side of the plunger-rod opposed to the first fixed stop means and on the opposite side of the actuating means to the advancing element so that said actuating means bears against said second stop means in said first position.

5. A device according to claim 3, comprising a second fixed stop means disposed on a side of the plunger-rod opposed to the first fixed stop means and on the opposite side of the actuating means to the advancing element so that said actuating means bears against said second stop means in said first position.

6. A device according to any one of the claims 1 to 5, comprising two end-of-travel stop means for an end portion of the plunger-rod opposed to said second end of the body.

7. A device according to any one of the claims 1 to 5, wherein the step-by-step advancing means comprise anti-return means cooperative with the plunger-rod to oppose the return of the plunger-rod when the actuating means is returned to said first position.

8. A device according to claim 7, comprising a thrid fixed stop means mounted on the body on one side of the plunger-rod, and a fourth fixed stop means mounted on the body on an opposite side of the plunger-rod to the third fixed stop means, the anti-return means comprising an anti-return member provided with an aperture and mounted on the plunger-rod with a small clearance between the plunger-rod and the anti-return member aperture, said anti-return member bearing, in a position thereof perpendicular to the plunger-rod, by a first side thereof facing said second end of the body on said third fixed stop means and bearing by a second side opposed to said first side of the anti-return member, against said fourth fixed stop means, a spring being engaged in a compressed state between the advancing element and the anti-return member so that the anti-return member is perpendicular to the plunger-rod when the actuating means is shifted away from said first position and is inclined when the actuating means is in said first position.

9. A device according to any one of the claims 1 to 5, comprising a case rigid with the body, the case extending said first end of the body, the plunger-rod extending through the case, and the case enclosing the advancing element and carrying said fixed stop means.

10. A device according to claim 9, comprising a laterally disposed handle on the case and a trigger carrying the actuating means disposed in the handle.

11. An artificial insemination device for small animals in combination with support means for the device, the device comprising a hollow cylindrical body, a plunger-rod slidably mounted in the body and projecting from a first end of the body, a periodic actuating means, a step-by-step advancing means cooperative with the plunger-rod and comprising an advancing element which is provided with an aperture and is mounted on the plunger-rod with a small clearance between the advancing element aperture and the plunger-rod and which bears against the periodic actuating means, which actuating means is mounted to be movable in translation relative to the body in a direction parallel to the plunger-rod between a first position and a second position, return means cooperative with the actuating means to return the actuating means to said first position, the hollow cylindrical body being adapted to receive at a second end thereof opposed to said first end a semen reservoir-tube, means associated with said second end of the body for maintaining the reservoir tube on the body, a stop means mounted to be adjustable in position relative to the body in a direction substantially parallel to the plunger-rod, said actuating means being in bearing relation to said stop means in second position, said support means comprising a support unit, a fixing unit for the body of the device mounted on the support unit to slide along a sliding axis, the body being disposed on the fixing unit in such manner that the plunger-rod is parallel to said sliding axis, a thrust unit rigid with the fixing unit, the thrust unit comprising a thrust member which would be disposed along said sliding axis substantially in lateral alignment with an orifice of a semen reservoir-tube when the reservoir-tube is mounted on the body, the periodic actuating means comprising a member which projects in a position of rest thereof from said first end of the body of the device and is located in confronting relation to a supporting stop means rigid with the support unit.

12. A device according to claim 11, wherein the thrust unit is mounted to be movable in translation relative to the fixing unit along said sliding axis, removable securing means being provided between the fixing unit and the thrust unit for rendering the thrust unit rigid with the fixing unit.

13. A device according to claim 11, comprising a yieldable return means cooperative with the fixing unit to bias the fixing unit forwardly of the support unit along said sliding axis, the fixing unit being mounted to be freely slidable rearwardly of the support unit against the action of the yieldable return means.

14. A device according to any one of the claims 11 to 13, wherein the thrust unit is mounted to be movable relative to the fixing unit in a transverse direction perpendicular to the plunger-rod.

15. A device according to any one of the claims 11 to 13, wherein the thrust member is mounted to be movable transversely of the plunger-rod.

16. A device according to any one of the claims 11 to 13, wherein the plunger-rod is disposed above said sliding axis.

17. A device according to claim 16, wherein the support unit comprises a part which is orientable about a horizontal axis perpendicular to the plunger-rod and to said sliding axis.

18. A device according to any one of the claims 11 to 13, wherein the fixing unit comprises a rod which is disposed on said sliding axis and is slidably mounted at one end in a tube which is part of the support unit and rigid at the other end of the rod of the fixing unit with the thrust unit.

19. A device according to claim 18, wherein the fixing unit comprises a block for fixing the body of the device, the block being rigid with the rod of the fixing unit but disposed outside the tube which is part of the support unit.

20. A device according to claim 18, wherein the thrust unit comprises a block which is slidably and rotatably mounted on an end portion of the rod of the fixing unit and a securing screw fixes the block on the rod of the fixing unit.

* * * * *